United States Patent
Vollenweider

(10) Patent No.: US 8,546,740 B2
(45) Date of Patent: Oct. 1, 2013

(54) EVALUATION OF A DIFFERENCE SIGNAL BETWEEN OUTPUT SIGNALS OF TWO RECEIVING DEVICES IN A SENSOR APPARATUS

(75) Inventor: Walter Vollenweider, Steinhausen (CH)

(73) Assignee: Siemens Aktiengesellschaft, Munich (DE)

( * ) Notice: Subject to any disclaimer, the term of this patent is extended or adjusted under 35 U.S.C. 154(b) by 368 days.

(21) Appl. No.: 12/735,844

(22) PCT Filed: Feb. 19, 2009

(86) PCT No.: PCT/EP2009/052002
§ 371 (c)(1),
(2), (4) Date: Nov. 19, 2010

(87) PCT Pub. No.: WO2009/103777
PCT Pub. Date: Aug. 27, 2009

(65) Prior Publication Data
US 2011/0108748 A1    May 12, 2011

(30) Foreign Application Priority Data
Feb. 19, 2008    (EP) ..................................... 08101743

(51) Int. Cl.
*G01V 8/00*    (2006.01)
(52) U.S. Cl.
USPC ........ 250/221; 250/222.1; 250/551; 340/630; 340/693.6
(58) Field of Classification Search
USPC .................. 250/221, 222.1, 222.2, 573, 574, 250/551; 340/628, 630, 693.6
See application file for complete search history.

(56) References Cited

U.S. PATENT DOCUMENTS

| | | | |
|---|---|---|---|
| 4,220,857 A * | 9/1980 | Bright | ..................... 250/339.15 |
| 4,857,895 A | 8/1989 | Kaprelian | |
| 5,352,901 A | 10/1994 | Poorman | |
| 5,493,119 A | 2/1996 | Törngren | |
| 6,611,320 B1 | 8/2003 | Lindberg et al. | |
| 2008/0258925 A1 | 10/2008 | Siber et al. | |

FOREIGN PATENT DOCUMENTS

| | | |
|---|---|---|
| DE | 102004001699 A1 | 8/2005 |
| EP | 0099729 A1 | 2/1984 |
| EP | 0877345 A2 | 11/1998 |
| GB | 2251682 A | 7/1992 |

* cited by examiner

*Primary Examiner* — Kevin Pyo
(74) *Attorney, Agent, or Firm* — Laurence A. Greenberg; Werner H. Stemer; Ralph E. Locher

(57) ABSTRACT

A sensor apparatus for optically detecting an object includes (a) a first emitting device, configured to emit a first emission beam, (b) a first receiving device, configured to receive a first reception beam, (c) a second receiving device, configured to receive a second reception beam, and (d) an evaluation unit connected downstream of the first receiving device and the second receiving device. The first reception beam and/or the second reception beam contains scattered light which is produced when an at least partial scattering of the first transmission beam occurs at the object. The evaluation unit is coupled to the first receiving device and the second receiving device so as to receive a difference signal between a first output signal of the first receiving device and a second output signal of the second receiving device. The sensor apparatus may be incorporated in a proximity sensor and a danger warning system.

14 Claims, 6 Drawing Sheets

EVALUATION OF A DIFFERENCE SIGNAL BETWEEN OUTPUT SIGNALS OF TWO RECEIVING DEVICES IN A SENSOR APPARATUS

BACKGROUND OF THE INVENTION

Field of the Invention

The present invention relates generally to the technical field of household technology. In particular, the present invention relates to a sensor apparatus for optically detecting an object, wherein the sensor apparatus comprises at least one transmitting device for transmitting a transmission radiation, and two receiving devices for receiving in each case a reception radiation. In this case, the reception radiation comprises a scattered light which is produced by at least partial scattering of the transmission radiation at the object that is to be captured. The present invention further relates to a proximity sensor and a hazard alarm, which comprise the cited sensor apparatus in each case.

Known photoelectrical proximity alarms or hazard alarms are sensitive to light which arrives in an optical receiver via a different path to that which was intended due to the reflection or scattering at the object that is to be recognized. It is possible for light, which is emitted by an optical transmitter of the alarm, to be reflected by the housing or by any objects that are situated in the detection region or in the active volume of the alarm and to arrive in the receiver. The presence of an object is simulated in this way. However, it is also possible for extraneous light to arrive in the receiver and override it, thereby preventing it from properly recognizing an object that is to be captured.

U.S. Pat. No. 5,352,901 discloses a smoke detector which utilizes the principles of both forward scattering and backscattering for the purpose of smoke detection. The smoke detector features two pairs comprising an optical transmitter and an optical receiver in each case. One optical receiver in each case is situated in the direct beam of an optical transmitter. By means of selectively activating the two optical transmitters, the continuous radiation and the scattered radiation can be detected independently of each other in a measured volume of the smoke detector.

The present invention addresses the problem of reducing the influence of interfering variables during the photoelectrical detection of an object, to the extent that reliable object detection can be achieved with a lower rate of false alarms.

BRIEF SUMMARY OF THE INVENTION

This problem is solved by the subject matter of the independent patent claims. Advantageous embodiments of the invention are described in the dependent claims.

According to a first aspect of the invention, a sensor apparatus for optically detecting an object is described. The sensor apparatus comprises (a) a first transmitting device, configured for transmitting a first transmission radiation, (b) a first receiving device, configured for receiving a first reception radiation, (c) a second receiving device, configured for receiving a second reception radiation, and (d) an evaluation unit which is connected behind the first receiving device and the second receiving device. The first reception radiation and/or the second reception radiation comprises a scattered light, which is produced in the event of at least partial scattering of the first transmission radiation at the object. According to the invention, the evaluation unit is coupled to the first receiving device and the second receiving device in such a way that the evaluation unit can be supplied with a difference signal between a first output signal of the first receiving device and a second output signal of the second receiving device.

The described sensor apparatus is based on the insight that a multiplicity of undesired interferences, which affect both receiving devices, can be elegantly eliminated or at least significantly reduced with regard to the strength of their effect by identifying a difference signal between the output signals of the two receiving devices. Such interferences can occur e.g. as a result of the unwanted receipt of extraneous radiation which is transmitted by an external radiation source and possibly overrides the relevant receiving device and/or an amplifier which is connected behind the receiving device. A further interference which can be at least reduced by means of the present invention might consist in the first transmission radiation being directed at least partially onto at least one of the two receiving devices by a reflection or scattering at an item that is situated in the spatial detection region of the described transmitting apparatus but does not represent the object to be detected. A similar interference can occur, for example, as a result of the transmission radiation being scattered and/or reflected at part of a housing of the sensor apparatus.

Particularly effective suppression of an interfering signal can be ensured if the transmission radiation that is transmitted by the first transmitting device, from the object that is to be detected, preferably falls on the one receiving device and does not, or only to a very limited extent, on the second receiving device.

In this document, the term radiation is understood to mean electromagnetic radiation of any wavelength. In particular, the electromagnetic radiation can be light in the visible, infrared or ultraviolet spectral range. In addition to a comparatively narrow-band spectral range or even a monochromatic radiation, the electromagnetic radiation can also comprise various wavelengths which represent a continuous spectrum or various discrete narrow-band and/or broadband spectral ranges. The electromagnetic radiation can also comprise wavelengths which are assigned to the far infrared and/or the far ultraviolet spectral range. In principle, microwave radiation or any other type of electromagnetic radiation can be used as a transmission radiation and correspondingly as a first and/or second reception radiation. Accordingly, the term "optical" relates to all cited spectral ranges of electromagnetic radiation and not solely to the visible spectral range.

According to an exemplary embodiment of the invention, the sensor apparatus further comprises a second transmitting device and a control device. The second transmitting device is configured for transmitting a second transmission radiation, wherein the first reception radiation and/or the second reception radiation comprises a scattered light which is produced by at least partial scattering of the second transmission radiation at the object. The control device is coupled to the first transmitting device and to the second transmitting device, and is configured such that the first transmitting device can be activated independently of the second transmitting device.

The first transmitting device can be assigned to the first receiving device in such a way that the first reception radiation is preferably detected by the first receiving device. This means that, in comparison with the second receiving device, the first receiving device detects a larger portion of the first reception radiation. The first reception radiation is preferably detected exclusively or at least mainly by the first receiving device. Correspondingly, the second transmitting device can be assigned to the second receiving device such that, in comparison with the first receiving device, the second receiving device detects a larger portion of the second reception radiation. The second reception radiation is preferably detected exclusively or at least mainly by the second receiving device.

The assignment of a transmitting device to the relevant receiving device can be done in particular by means of the relative spatial arrangement and/or by means of the relative spatial alignment of the preferred transmission direction of the relevant transmitting device and the preferred reception direction of the corresponding receiving device.

The control device can feature a driver circuit, for example, which is coupled to the first transmitting device and to the second transmitting device. The driver circuit can be configured such that only the first transmitting device can be activated in a first time segment, and only the second transmitting unit can be activated in a second time segment.

The first time segment and the second time segment can be separated from each other such that there is no temporal overlap with regard to the activation of the two transmitting devices. In this case, the two time segments can follow each other immediately or with a specific time interval.

By means of an alternating or temporally opposite-phase activation of the two transmitting devices, the two reception radiations can easily be differentiated from each other. Since only one transmission radiation and the corresponding reception radiation are ever present at any instant, it is easy to achieve a permanent assignment of the first transmitting device to the first receiving device and the second transmitting device to the second receiving device.

The control device and/or the driver circuit can comprise e.g. a signal source which is coupled via a non-inverting element to the first transmitting device and via an inverting element to the second transmitting device. In particular, the signal source can be a rectangular signal generator. The non-inverting element can be a conventional non-inverting amplifier, while the inverting element can be an inverting amplifier.

By independently triggering the two transmitting devices, the described sensor apparatus can be operated in various operating modes. An asymmetric operating mode is possible, for example, in which both the first receiving device and the second receiving device are active, while only one of the two transmitting devices is switched on and the other is selectively switched off. If both receiving devices show at least approximately the same signal in this operating mode, it is a remote echo. This can be cause by a reflection of the transmission radiation, which was transmitted by the active transmitting device, on a remotely distant item such as e.g. the floor of a monitored space. In a hazard situation, in which smoke intrudes into or originates in the monitored space, the smoke will also intrude into the vicinity of the sensor apparatus, such that the two receiving devices receive a very different scatter signal. In this case, the receiving device that is assigned to the switched-on transmitting device will receive a much more intensive reception radiation than the other receiving device.

According to a further exemplary embodiment of the invention, the sensor apparatus additionally comprises a switch element which is coupled to the first transmitting device in such a way that the first transmitting device can be deactivated.

The described sensor apparatus can therefore be operated in two different operating modes. In a first operating mode, the switching element is closed and the first transmitting device can be activated. A first difference signal can be determined in this case. In a second operating mode, the switching element is open and the first transmitting device is and/or remains switched off in any case. A second difference signal can be determined in this case.

On the basis of the first difference signal and the second difference signal, possibly using suitable algorithms which are applied e.g. in the evaluation unit, it is possible to draw conclusions relating to the size and/or the spatial position of a recognized object.

It should be noted that a further switching element can obviously also be provided, by means of which the second transmitting device can be deactivated.

According to a further exemplary embodiment of the invention, the sensor apparatus additionally comprises a balancing element which is arranged in a transmit-signal path to the first transmitting device or in a receive-signal path from the first receiving device, and which can be varied such that the difference signal can be adjusted to a predefined value.

The described use of at least one balancing element has the advantage that long-term fluctuations and/or drifts in the strength of the transmission radiation or the strength of the first output signal can be reliably equalized. This also applies to scattering items which are not stationary within or outside of the detection region of the sensor apparatus, and which possibly contribute to a difference of the two output signals and hence to an offset in the difference signal even without the presence of an object that is to be detected.

In this context, the transmit-signal path can be understood to be that part of an electronic circuit by means of which the transmitting device is triggered. Consequently, the transmit-signal path can extend in particular between a transmit-signal generator and the transmitting device. A driver circuit can also be assigned to the transmit-signal path.

In this context, the receive-signal path can be understood to be that part of an electronic circuit by means of which the output signal of the corresponding receiving device is detected. Consequently, the receive-signal path can extend between the receiving device and the evaluation unit. However, the balancing element is preferably arranged between the receiving device and that element of the sensor apparatus in which the difference between the two output signals is identified.

It should be noted that provision can also be made for a further balancing element, such that a balancing element is located in both the transmit-signal path and the receive-signal path, and these paths can be balanced independently of each other. A further balancing element can also increase the adjustment range, such that even large differences between the two output signals can be equalized.

In particular, if the sensor apparatus comprises the above described second transmitting device, provision can also be made for further balancing elements, these being arranged e.g. in a transmit-signal path to the second transmitting device and/or in a receive-signal path from the second receiving device.

In particular, the predefined value of the difference signal can be a voltage level of 0V or a current intensity of 0 mA. The described balancing can be carried out e.g. under defined test conditions, in which it is ensured that no object is present in the detection region of the sensor apparatus.

Suitable algorithms, which are applied e.g. in the evaluation unit, can be used for adjusting the difference signal. The balancing of the two output signals can be carried out automatically in this way. It need only be ensured that suitable test conditions are present during the balancing and, in particular, that no object to be detected is present in the detection region of the sensor apparatus.

According to a further exemplary embodiment of the invention, the evaluation unit is configured in such a way that a direct-current part of the difference signal and an alternating-current part of the difference signal can be identified.

Since the alternating-current part can also be used to identify an amplitude of the alternating-current part of the difference signal, at least in the context of periodic modulation, it is easy to work out the ratio of the amplitude of the alternating-current part to the value of the direct-current part, wherein this can likewise take place in the evaluation unit or in a separate analysis unit. On the basis of this ratio, e.g. with the aid of suitable algorithms, it is possible to draw conclusions relating to the type of object that has been recognized and/or the speed at which the object is moving through the detection region, into the detection region or out of the detection region. In particular, it is possible reliably to distinguish between physical interferences such as the unwanted intrusion of insects into the detection region of the sensor apparatus, for example, and an object that is to be detected. In this case, it can be advantageous to know at least approximately the shape and/or the scattering power of the object to be detected. For example, the object to be detected can be a person who is standing in front of an automatic door and waiting to be admitted.

However, the described sensor apparatus can be optimized for the detection of smoke. In this case, the sensor apparatus is a smoke alarm.

It should be noted at this point that the evaluation unit can also be configured such that, on the basis of the temporal profile and/or the strength of the two output signals, it is possible to identify the size of the object to be detected. Therefore, for example, a first type of notification can be output in the event of intrusion of an object whose size is greater than a predetermined limit, and a second type of notification can be output in the event of intrusion of an object whose size is less than a predetermined limit.

According to a further exemplary embodiment of the invention, the first receiving device and the second receiving device are arranged and aligned relative to each other in such a way that (a) in the event of scattering of the first transmission radiation at the object for a given environmental radiation, the first output signal of the first receiving device differs from the second output signal of the second receiving device, and that (b) these output signals differ less after the object moves away from the sensor apparatus for the same environmental radiation.

It should be noted that the given environmental radiation can have an infinitely low intensity, or even an intensity of "zero", at least at the location of the sensor apparatus or at the location of the two receiving devices. This can mean that, with the exception of the reception radiations which are produced by a scattering of the first and/or second transmission radiation, no further radiation is detected by the sensor apparatus.

The first receiving device and the second receiving device can also be arranged and aligned relative to each other in such a way that (a) insofar as the object is situated at a first distance from the sensor apparatus, the first output signal and the second output signal are different, and (b) insofar the object is situated at a second distance from the sensor apparatus, which is greater than the first distance, the first output signal and the second output signal differ less.

It should be noted here that, in the case of a relatively close object, the scattered light comprises a significant portion of the first reception radiation. In the case of a relatively remote object, the scattered light can strike the first receiving device and the second receiving device with at least approximately identical intensity. Likewise, in the case of a remote object, it is nonetheless also possible for the scattered light to have only a very small or even vanishingly small portion of the radiation intensity striking the first and/or the second receiving device. Therefore, for example, the majority of the striking radiation intensity can come from an external interference radiation source, whose radiation directly or indirectly strikes the two receiving devices with at least similar intensity from far away.

The arrangement and the alignment of the transmitting device and the two receiving devices can be such that the first transmission radiation is preferably emitted in a first direction, which is directed away from the detection region of the second receiving device. In this way, it can be ensured that little or no scattered radiation from a nearby object strikes the second receiving device, and significantly more or a clearly more intensive scattered radiation strikes the first receiving device. This has the advantage that, as a result of working out the difference between the first output signal and the second output signal as described above, interferences which are produced by an external interference radiation source are automatically eliminated and need no longer be taken into consideration by the evaluation unit during the subsequent signal evaluation.

The external interference radiation source can be the sun, for example, directing solar radiation onto the described sensor apparatus directly or indirectly.

If the sensor apparatus also comprises a second transmitting device, the first transmission radiation can also be emitted at least approximately parallel to the second transmission radiation. If the first receiving device is then arranged close to the first transmitting device and the second receiving device is then arranged close to the second transmitting device, the first receiving device will then essentially be assigned to the first transmitting device and the second receiving device will then essentially be assigned to the second transmitting device.

In this case, in particular, the two receiving devices can be so distant from each other that the first reception radiation is not detected by the second receiving device and the second reception radiation is not detected by the first receiving device in the case of normally detected objects. In the case of an interference radiation source which is relatively distant from the sensor apparatus, the interference radiation can strike the first receiving device and the second receiving device at least approximately equally when averaged over time. As a result of working out the difference as described, the influence of the interference radiation is automatically eliminated or at least significantly reduced already before any signal processing.

According to a design variant, the first transmitting device comprises at least two transmitting elements and/or at least one of the two receiving devices comprises at least two receiving elements. The realization of the first transmitting device, the first receiving device and/or the second receiving device comprising a plurality of individual transmitting or receiving elements has the advantage that a highly efficient transmitting or receiving device can be constructed easily and economically, wherein the available energy is utilized particularly effectively. In this case, the individual sending and/or receiving elements can be combined together in a series and/or parallel connection. In this case, the combined transmitting elements are preferably arranged relative to each other such that their transmitted partial transmission beams overlap as far as possible and therefore produce an intensive transmission radiation. Correspondingly, the combined receiving elements are preferably so arranged, relative to each other, that they detect the relevant reception radiation as efficiently as possible.

According to a further design variant, the second transmitting device comprises at least two transmitting elements. The same then applies to the preferred relative arrangement of the two transmitting elements as to the at least two transmitting elements which, in combination with each other, form the first transmitting device.

According to a further design variant, the first receiving device and/or the second receiving device comprises at least one semiconductor detector, in particular a PIN diode. This has the advantage that the at least one optical receiving device can be realized economically, is highly sensitive and can easily be configured into an electronic circuit arrangement.

According to a further exemplary embodiment of the invention, a subtraction unit is coupled on the input side to the first receiving device and the second receiving device and on the output side to the evaluation unit. The subtraction unit can be configured for working out the difference signal on the basis of the two output signals. The subtraction unit can be realized by means of one or more operation amplifiers, by means of inverse-coupled difference amplifiers or by means of a discrete electronic circuit, for example.

The output signals of the two receiving devices can be supplied directly to the subtraction unit. Alternatively, at least one of the two output signals can also be suitably amplified and/or filtered by means of an electronic filter, such that the difference is only worked out subsequently using a suitable subtractor.

The subtraction unit can be realized e.g. by means of suitable hardware components which determine a difference signal between the first output signal and the second output signal on the basis of analog output signals of the two receiving devices. This difference signal can be suitably evaluated by a processor in the evaluation unit.

The subtraction unit can likewise be integrated in the evaluation unit, and be realized there by means of hardware, by means of software, or by means of a combination of hardware and software.

As a result of evaluating a difference signal, it is possible e.g. to eliminate the influence of extraneous light sources which irradiate external light into the two receiving devices and, thereby producing a falsely increased output signal for each individual receiving device.

According to a further exemplary embodiment of the invention, the first receiving device and the second receiving device are wired together in parallel with reversed polarity. This means that the receiving device can also feature in particular or solely those electrical lines which effect the parallel circuit of the two receiving devices. It is therefore advantageously possible to work out the inventive difference signal without further instrumental precautions, and already before the supply of the first and/or second output signal to an amplifier circuit.

According to a further exemplary embodiment of the invention, the sensor apparatus additionally comprises a base element with a plane assembly surface, wherein the first transmitting device, the first receiving device, a second transmitting device which is configured for transmitting a second transmission radiation, and the second receiving device are mounted on the assembly surface. In this case, the first receiving device is arranged near to the first transmitting device and is configured for receiving the first reception radiation, this resulting from a backscattering of the first transmission radiation at an object of measurement which is situated in a first detection space. Furthermore, the second receiving device is arranged near to the second transmitting device and is configured for receiving the second reception radiation, this resulting from a backscattering of the second transmission radiation at an object of measurement which is situated in a second detection space.

The described sensor apparatus can therefore be realized by means of a plane arrangement of all optoelectronic components on a shared assembly surface in a particularly flat structural shape.

If the sensor apparatus is used for the detection of smoke, it is preferable to detect those smoke particles which are situated in the immediate vicinity of the sensor apparatus, since only those smoke particles contribute significantly to the generation of reception radiation.

With this in mind, the two terms "detection space" and "field of view of the sensor apparatus" are distinguished from each other in this application.

In this case, the term "detection space" is understood to be a layer which immediately adjoins the sensor apparatus. Smoke which is situated within the detection space will then result in a significant and measurable scatter signal. Smoke which is situated outside of the detection space and which is therefore further away from the sensor apparatus will not contribute significantly to the received backscatter signal.

The term "field of view of the sensor apparatus" is understood to be the region which is generally detected by the sensor apparatus and which lies outside of the detection space. As explained above, it can occur that smoke which is situated in the field of view of the smoke alarm does not contribute significantly to the scatter signal. However, this does not apply to physical scattering objects such as insects or pieces of furniture, for example. These can result in a significant scatter signal even if they are merely in the field of view of the sensor apparatus.

As a result of the flat structural shape, it is possible to integrate the described sensor apparatus without great expense into the wall and in particular into the ceilings or spaces that are to be monitored. The described sensor apparatus can also be mounted on walls and/or ceilings easily in the case of surface assembly. In this case, the sensor apparatus only occupies a small space requirement. Moreover, the described sensor apparatus can be mounted discreetly, in such a way that it is not noticed by people in the space that is monitored by the sensor apparatus, or at least is not noticed as disruptive to the room layout.

If the sensor apparatus is a smoke alarm, the object to be detected is smoke, which comprises individual smoke particles that are detected by the described smoke alarm, this being based on the scattered radiation principle. In practice, however, the object to be detected can also be another object, e.g. an insect or an item that is inadvertently brought into the detection space, which likewise generates a scatter or backscatter signal. The backscatter signals from physical objects located in the detection space, in particular insects, are nonetheless significantly stronger in comparison with the optical backscatter signals caused by smoke. By means of suitable assessment of the output signals of the first and second receiving device by the evaluation unit, however, such results can be reliably distinguished from the actual presence of smoke.

If the sensor apparatus is operated in backscatter geometry, lens systems for the transmitting devices and/or receiving devices are advantageously not required. As a result of this, the described sensor apparatus can be manufactured particularly economically and is also suitable as a low-cost mass product for monitoring private spaces.

In the case of the described detector, the measurement of the scattered radiation can be done using a backscatter geometry of approximately 180°. The deviation of the scatter angle from an exact backscatter and hence from exactly 180° is produced (a) from the separation between the first and second transmitting device, and the first and second receiving device and (b) from the distance of the location of the backscattering from the relevant transmitting device or receiving device. For an occurrence of scattering at a scattering object which is located in the detection space, a small layer thickness of the detection space can result in a clear deviation of the scatter angle from 180°.

The described sensor apparatus differs from conventional smoke alarms particularly in the backscatter geometry that is used, wherein conventional smoke alarms either as forward scatterers have a scatter angle of approximately 60° or as backscatterers have a scatter angle of approximately 120° between illumination light and scattered light.

The optoelectronic or photoelectronic components of the sensor apparatus or smoke alarm can advantageously be semiconductor diodes which are mounted using surface mount technology. In this case, the base element can be a printed circuit board or at least feature a printed circuit board on which semiconductor transmitting diodes and semiconductor receiving diodes are mounted and electrically contacted in a known manner.

According to a further exemplary embodiment of the invention, the first transmitting device and the first receiving device are realized by a first reflective light barrier and/or the second light transmitter and the second light receiver by a second reflective light barrier. This has the advantage of allowing commercially available reflective light barriers to be used. No relative adjustment between a transmitting device and the corresponding receiving device for matching the radiation direction of the transmitting device to the reception direction of the receiving device is required, by virtue of the fixed relative arrangement of these optoelectronic components within a common component or at least within a common housing. The sensor apparatus can thus be constructed in an advantageous manner with a small installation expense.

According to a further exemplary embodiment of the invention, the direction of the first transmission radiation is inclined relative to a normal of the assembly surface in the direction of the first receiving device and/or the direction of the second transmission radiation is inclined relative to the normal of the assembly surface in the direction of the second receiving device.

In this context, the term direction signifies the mean radiation direction of the first and/or second transmitting device. This means that the transmitting devices need not only be lasers such as a VCSEL (Vertical Cavity Surface Emitting Laser), which emit an almost parallel light bundle. The transmitting devices can also have a radiation characteristic with diverging light beams which have a certain angular distribution around the corresponding mean radiation direction that is inclined to the respective receiving device.

According to a further exemplary embodiment of the invention, the direction of the first transmission radiation and the direction of the second transmission radiation run parallel to each other.

In this case, two spatially discrete detection spaces can arise, whose separation depends on the distance between the two transmitting devices on the assembly surface of the base element.

In the case of diverging or widened light beams for the first and/or second transmission radiation, the direction of the transmission radiation relates to the mean radiation direction in each case.

According to a further exemplary embodiment of the invention, the first transmitting device and the second transmitting device and the first receiving device and the second receiving device represent an external boundary of the sensor apparatus. This means that neither the transmitting devices nor the receiving devices are located within a housing of the sensor apparatus. Consequently, no other parts of the described sensor apparatus are situated outside of the photoelectrical components (transmitting device and receiving device). This also applies to covers or housing parts. The sensor apparatus can therefore be designed such that no further (possibly optically transparent) covering, by means of which the photoelectrical components are protected against soiling, is located between the photoelectrical components and the relevant detection space. Such covers or contamination shields are not required at all for many applications however, especially in the domestic environment.

Furthermore, the first detection space and/or the second detection space can also be situated outside the sensor apparatus. In this case, the sensor apparatus is an open smoke alarm which does not have its own optical chamber.

According to a further exemplary embodiment of the invention, the first receiving device is configured for detecting a temporal profile of the first reception radiation.

By detecting the scattered radiation that is detected by the first receiving device as a function of the time, it is easy to obtain information about a scattering object that intrudes into the first detection space. If the intruding scattering object is indeed smoke, the change of the scattered radiation over time will take place relatively slowly, since smoke usually intrudes continuously into the detection space. By contrast, a physical object such as e.g. an insect or an item which is inadvertently brought into the field of view of the sensor apparatus by a person, will essentially cause an abrupt change in the scattered radiation intensity. Consequently, with reference to the degree of change relative to time in the scattered radiation intensity that is detected by the first receiving device, reliable information about the type of the object can be obtained.

According to a further exemplary embodiment of the invention, the first transmitting device is configured for transmitting a pulsed first transmission radiation.

The use of pulsed transmission radiation with very short pulses having a temporal length of preferably less than 1 ns in connection with a receiving device which has a temporal resolution that is likewise in the nanosecond range has the advantage that information can be obtained about the spatial distribution of the scattering objects. In this case, e.g. a first optical reflection signal, which comes from the floor of a smoke alarm that is arranged on the ceiling of a space, can be temporally distinguished from a second reflection signal which comes from a scattering at smoke. In this case, the fact is exploited that smoke only delivers a significant reflection signal if it is situated within a detection space that is near to the smoke alarm. A backscatter light that is assigned to the smoke can then be assigned an insignificant light delay time. By contrast, for the backscatter light which comes from the floor of the monitored space, a finite light delay time that is defined by the distance between the smoke alarm and the floor is measured. This exploits the fact that the light path, which is predetermined by the speed of light and covers one light pulse within one nanosecond, is 30 cm long.

In this context, it should be noted that the detection space can be a layer which is situated immediately below the smoke alarm, this being typically arranged on the ceiling of a space. The layer thickness of the detection space can be approximately 10 mm, for example.

Light which is scattered at smoke therefore has a signal path of approximately 5 to 20 mm. This results in a signal delay of 17 to 67 picoseconds. In other words, the smoke signal has only an insignificant and unmeasurable time delay, and likewise has a signal dispersion which cannot be measured at acceptable expense. However, interfering physical scattering objects that are more distant can be distinguished from backscattering at smoke near the smoke alarm using the light delay time if the corresponding light receiver has sufficient temporal resolution. For example, an item which is 15 cm distant from the sensor apparatus or the smoke alarm, apart from a very strong signal, also produces a measurable signal delay of one nanosecond. In addition, pulse widening can also occur if the item actually comprises a plurality of backscatter regions which are situated at different distances from the smoke alarm.

For example, from a pulse duration of the received scattered radiation, which pulse duration is longer than the pulse duration of the corresponding transmission radiation, it is possible to conclude that the transmission radiation is backscattered at various items which are located at different distances from the sensor apparatus. Such a temporal widening or structuring of the reception radiation pulses, this being caused by different items, is therefore a reliable indicator that the scattering object located in the detection space is not smoke, but is a reflection on the floor or other nearby items.

By contrast, smoke does not result in a measurable pulse widening. This also applies if only low-cost components are used for the smoke alarm and no optical high-performance measuring instruments are used for measuring delay times in the picosecond or femtosecond range. This means that, with reference to the pulse length and pulse structure of the received scattered radiation signal, physical items such as e.g. insects or items that are inadvertently brought into the field of view of the smoke alarm can reliably be distinguished from smoke which is in the detection space.

In addition, by means of a measurement of the time difference t between the transmission of a transmission radiation pulse and the backscattered scattered radiation pulse that is detected by the receiving device, it is possible to identify how far distant the relevant item is from the transmitting device or the receiving device. In this case, the distance s between the item and the sensor apparatus is given by the following equation:

$$s = c \cdot t/2$$

where c represents the speed of light.

It should be noted that the second transmitting device can obviously also be configured for transmitting pulsed transmission radiation. Likewise, the second receiving device can be configured for detecting a temporal profile of the second reception radiation.

Aspects relating to the method of the invention are described below.

A method for detecting smoke using the above described sensor apparatus or the above described smoke alarm comprises (a) transmitting at least the first transmission radiation by means of the first transmitting device and (b) receiving at least the first reception radiation by means of the first receiving device, wherein the reception radiation results from a backscattering of the first transmission radiation at an object which is located in a first detection space.

The described method is based on the insight that reception radiation that is received in a backscatter geometry can also produce sufficiently strong signals to allow evaluation for a reliable detection of smoke. By virtue of this insight, which has been verified by the inventors by means of experimental trials, it is now possible to realize smoke alarms within a particularly compact structural shape. In this case, the photoelectrical components can be arranged on a shared printed circuit board.

According to a further exemplary embodiment of the invention, the method additionally comprises receiving the second reception radiation by means of the second receiving device.

If only one of the two receiving devices is activated, reliable detection of smoke can take place by means of a coordinated evaluation of the reception intensities measured by the two receiving devices. As explained above, due to a backscattering at spatially distributed smoke particles, the reception radiation received by the first receiving device will be significantly greater than the radiation intensity which strikes the second receiving device, which is assigned to the non-activated transmitting device. Only in the case of scattering at a very distant item will the two intensities, each of which strikes one of the two receiving devices, be at least approximately the same.

According to a further exemplary embodiment of the invention, the first transmission radiation features radiation pulses. By virtue of the first transmitting device introducing a time dependency of the transmission radiation, it is possible to obtain additional information relating to the spatial position of scattering objects that are located in the first detection space or in a field of view of the sensor apparatus or of the smoke alarm, said field of view being assigned to the first transmitting device and the first receiving device.

The second transmission radiation, which is transmitted by the second transmitting device, can obviously also feature radiation pulses.

According to a further exemplary embodiment of the invention, the method additionally comprises measuring the length of the radiation pulses which are backscattered as first reception radiation. This has the advantage that information can be obtained relating to the spatial arrangement of various items within the field of view of the smoke alarm.

Depending on the pulse length, a wide spatial distribution of the scattering objects therefore results in a temporal widening or structuring of the backscattered reception radiation pulses in comparison with the transmitted transmission radiation pulses. This is because the transmission radiation is backscattered at various items which are at different distances from the sensor apparatus. Bearing in mind the finite speed of light, different optical distances result in a temporal widening or structuring of the received reception radiation pulses. By contrast, a backscattering at smoke will result in no clear lengthening of the reception radiation pulses in relation to the transmission radiation pulses. As explained above, this is because only smoke which is in the immediate vicinity of the smoke alarm in the detection space will deliver a significant backscatter signal. Smoke which is merely in the field of view of the smoke alarm usually delivers a backscatter signal that cannot be measured. On the basis of the pulse length and the pulse structure of the received reception radiation, it is therefore possible reliably to distinguish between physical items such as e.g. insects or items which are inadvertently brought into the field of view of the alarm and smoke which intrudes into the detection space.

It should be noted that the temporal lengths of radiation pulses that are backscattered as second transmission radiation can obviously also be measured and evaluated correspondingly.

According to a further exemplary embodiment of the invention, the method additionally provides for measuring the time difference between the transmission of a pulse of the first transmission radiation and the receipt of the corresponding pulse of the backscattered first reception radiation. This has the advantage that the distance of a scattering object from the first transmitting device or the first receiving device can be identified absolutely.

Of course, the time difference between the transmission of a pulse of the second transmitting device and the receipt of the corresponding pulse of the backscattered second reception radiation can also be measured in a corresponding manner.

According to a further aspect of the invention, a proximity sensor for optically detecting the presence of an object in a detection region is described. The proximity sensor comprises a sensor apparatus of the type described above.

The described proximity sensor is based on the insight that the above described optical sensor apparatus is especially suitable for detecting the intrusion of objects into the detection region.

In the field of household technology, the proximity sensor can be used e.g. to initiate automatic door opening and/or closing if a person is to enter a room or if the doors of the room are to be closed again. In this case, the proximity sensor is configured and arranged such that the detection region is situated in front of the door concerned.

It should be noted that, particularly in the field of household technology, the proximity sensor is also often referred to as approach sensor, proximity alarm and/or approach alarm.

The proximity sensor can also be a so-called intrusion alarm, which detects the unwanted intrusion of an unauthorized person and/or object into a monitored region. In this case, the sensor apparatus that is used can also work according to the principle of a reflective light barrier. The proximity sensor can therefore be arranged in a container such as a showcase, for example, and indicate any unauthorized removal of an item that is located in the showcase. Interfering reflections caused by a facing glass panel, for example, are automatically reduced at least to a large extent by working out the difference in accordance with the invention.

According to a further aspect of the invention, a hazard alarm for recognizing a hazard situation is described, said hazard alarm being particularly suitable for detecting smoke in a monitored smoke. The described hazard alarm comprises a sensor apparatus of the type described above.

The described hazard alarm is also based on the insight that the above-described optical sensor apparatus is particularly suitable for reliably recognizing a hazard situation.

Therefore the described hazard alarm can also be a fire alarm which detects a build up of smoke gas in the event of a fire. In this case, the described object is smoke or individual aerosols or smoke particles. Of course, the hazard alarm can also recognize the occurrence of smoke independently of a fire. For the purpose of smoke detection, the hazard alarm can make use of the known scattered light principle.

It should be noted that embodiments of the invention are described with reference to different subject matter of the invention. In particular, certain embodiments of the invention are described in relation to apparatus claims and other embodiments of the invention are described in relation to method claims. However, when reading this application, it will immediately be clear to a person skilled in the art that unless explicitly indicated otherwise, in addition to a combination of features belonging to, one type of subject matter of the invention, any combination of features belonging to different subject matter of the invention is also possible.

Further advantages and features of the present invention are derived from the following exemplary description of presently preferred embodiments. The individual figures in the drawing of this application are merely intended to be schematic and are not to scale.

DESCRIPTION OF THE INVENTION

It should be noted that features or components of different embodiments, which are identical or at least functionally identical to the corresponding features or components according to the embodiment, are denoted by the same reference signs. In order to avoid unnecessary repetition, features or components which have already been explained with reference to a previously described embodiment are not explained again in detail at a later point.

It should also be noted that the embodiments described below merely represent a limited selection of possible design variants of the invention. In particular, it is possible to combine the features of individual embodiments in a suitable manner, such that a person skilled in the art will consider a multiplicity of different embodiments to be clearly disclosed on the basis of the design variants that are explicitly illustrated here.

Figure 1:
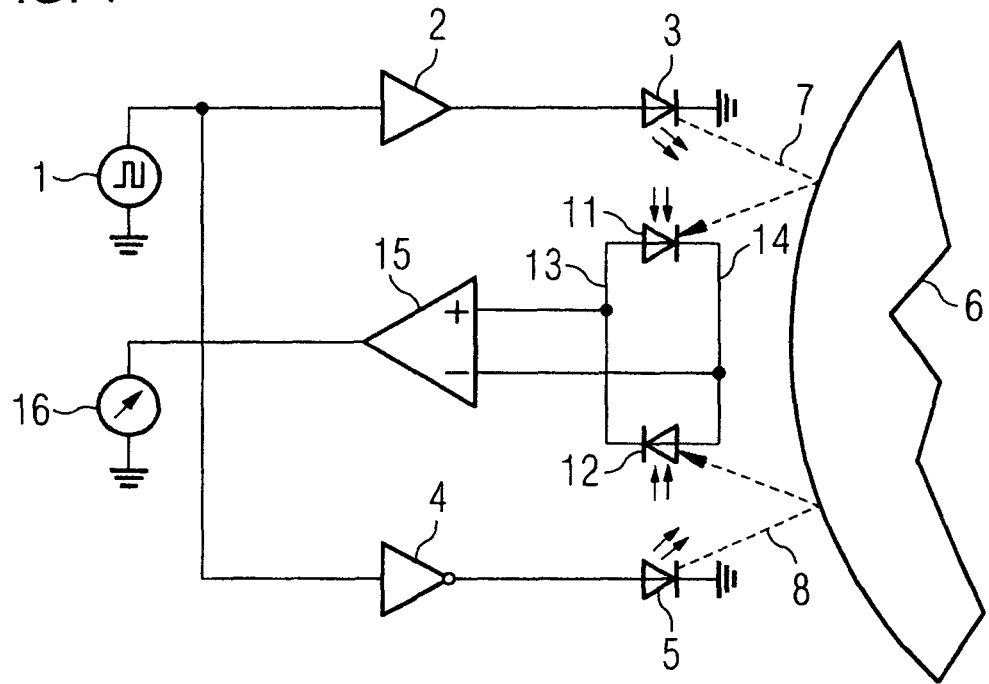
FIG. 1 shows a sensor apparatus according to a first exemplary embodiment of the invention, comprising two receiving devices in the form of photodiodes which are wired together in parallel with reversed polarity, during the detection of a comparatively close scattering object.

FIG. 1 shows a first exemplary embodiment of a sensor apparatus. The sensor apparatus comprises a signal source 1. According to the exemplary embodiment illustrated here, the signal source is a function generator 1, which outputs a rectangular voltage. If a rectangular voltage of a defined frequency is used, the circuit of the sensor apparatus can be constructed in a particularly simple manner. However, it is also possible in principle to use a voltage of any type, even with an irregular time profile.

The voltage of the signal source 1 is supplied to a non-inverting amplifier 2, where it is amplified to the extent that the output signal of the amplifier 2 is capable of supplying a first optical transmitting device 3 with a current that is sufficiently high for the correct operation of the optical transmitting device 3. According to the exemplary embodiment illustrated here, the first optical transmitting device is a first light-emitting diode 3.

The voltage of the signal source 1 is likewise supplied to an inverting amplifier 4, where it is amplified to the extent that the output signal of the amplifier 3 is capable of supplying a second optical transmitting device 5 with a current that is sufficiently high for the correct operation of the transmitting device 5. According to the exemplary embodiment illustrated here, the second optical transmitting device is a second light-emitting diode 5.

As a result of using the inverting amplifier 4 and the non-inverting amplifier 2, the current flow through the first light-emitting diode 3, and hence also the first transmitted light 7 that is transmitted from the first light-emitting diode 3, is temporally in opposition of phase relative to the current through the second light-emitting diode 5, and hence also relative to the transmitted light 8 that is transmitted from the second light-emitting diode 5. This means that as the light-emitting diodes 3, 5 only emit light 7, 8 when they are exposed to current in a conducting direction, the first light-emitting diode 3 will emit the light 7 and the second light-emitting diode 5 will be switched off during a first phase. Correspondingly, during a second phase the second light-emitting diode 5 will emit the light 8 and the first light-emitting diode 3 will be switched off.

If an object to be detected is present in the active volume of the sensor apparatus, said volume also being referred to as detection region of the sensor apparatus in this document, the light which is transmitted from the two light-emitting diodes 3 and 5 is reflected or scattered. The object 6 can be e.g. a person who is seeking admission to a space that is still closed by a door. However, the object 6 can likewise be an burglar or even a burglary tool of a burglar.

It can be seen from FIG. 1 that the light 7 from the first light-emitting diode 3 preferably arrives in the first optical receiving device 11, and the light 8 from the second light-emitting diode 5 preferably arrives in the second optical receiving device 12. According to the exemplary embodiment illustrated here, the first optical receiving device is a first photodiode 11 and the second optical receiving device is a second photodiode 12.

However, it should be noted that it is not at all necessary for the two optical paths between the first light-emitting diode 3 and the first receiving device 11 and between the second light-emitting diode 5 and the second receiving device 12 to be entirely separate from each other.

According to the exemplary embodiment illustrated here, the first photodiode 11 is wired to the second photodiode 12 in an antiparallel manner via electrical lines 13 and 14. Consequently, the current that can be consumed by these two lines corresponds exactly to the difference in current that occurs in the two individual photodiodes 11 and 12 during the detection of the light that is backscattered from the object 6.

The two lines 13 and 14 are wired to the inputs of a difference amplifier 15, which therefore generates an image of the current between the two lines 13 and 14. The image can be proportional to the difference current. However, it is also possible to use a logarithmic amplifier, for example, if the sensor apparatus is to have a particularly large dynamic range, for example. The difference amplifier 15 is preferably a so-called transimpedance amplifier with a small input impedance, which generates at its output a voltage which is proportional to the value of the transimpedance and also proportional to the current between the two lines 13 and 14 and hence to the difference of the currents in the photodiodes 11 and 12. As a result of using a transimpedance amplifier, the influence of the capacitances of the photodiodes 11, 12 and/or of the connection lines 13, 14 can be rendered largely ineffective. However, it is also possible to use any other type of difference amplifier if the influence of the parasitic capacitances, particularly of the photodiodes 11, 12 and the lines 13, 14, does not become too great in the subsequent signal processing.

The output signal of the difference amplifier 15 is supplied to an evaluation unit 16, which is drawn as a measuring device for simplicity in FIG. 1. The evaluation unit 16 has the task of determining, on the basis of the incoming signal which is output by the difference amplifier, whether an object that is to be detected is present in the detection region. If this is the case, the evaluation unit 16 initiates a corresponding notification.

If it is necessary merely to recognize the object 6, and no further demands are made of the signal evaluation of the sensor apparatus, the operation of the sensor apparatus is very similar to that of a conventional reflective light barrier. There are then no essential advantages in the simple recognition of the object 6. However, if interferences are present, this frequently being the case in practice, particular advantages are derived from the described circuit arrangement and in particular from the direct processing of the difference signal between both photodiodes 11 and 12.

For example, it can occur that the photodiodes 11 and/or 12 receive light from a far distant item, which is actually located outside of the normal detection region and should not actually be significant to the sensor apparatus. This is illustrated schematically in FIG. 2.

Figure 2:
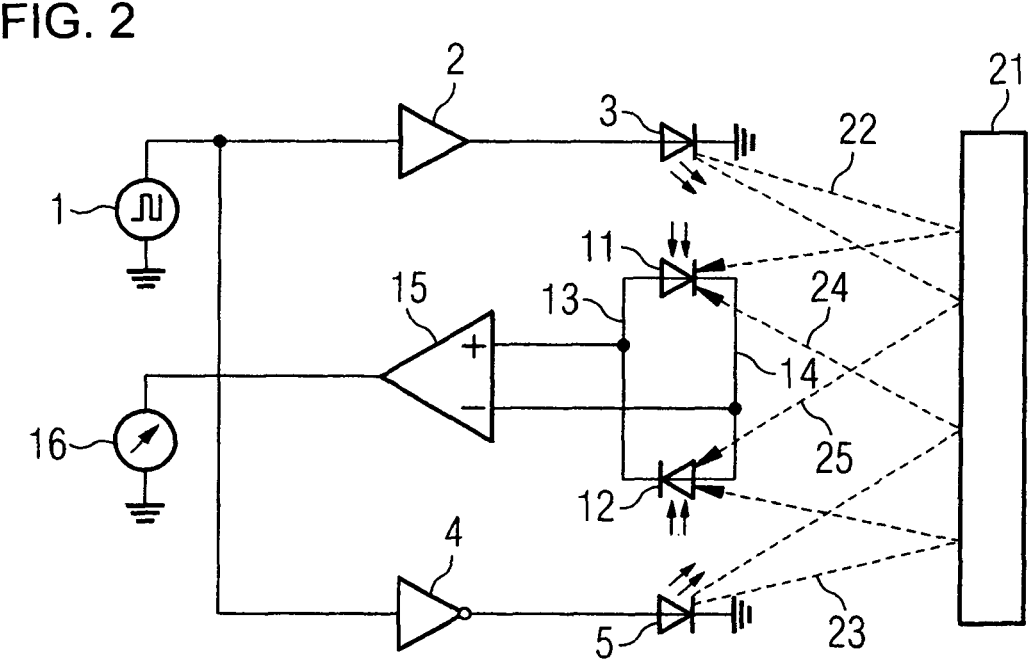
FIG. 2 shows the sensor apparatus as illustrated previously in FIG. 1, during the detection of a comparatively distant reflecting item.

FIG. 2 shows the sensor apparatus already illustrated in FIG. 1 during the detection of a comparatively distant reflecting item 21. As a result of the high reflectivity of the item 21, which can be e.g. the glass panel of a showcase, a significant portion of light strikes the photodiodes 11 and 12. In particular, light from the first light-emitting diode 3 arrives in the first photodiode 11 via the beam path 22. Likewise, light from the second light-emitting diode 5 arrives in the second photodiode 12 via the beam path 23, in a similar manner to that shown above in FIG. 1.

In addition, however, light from the first light-emitting diode 3 also arrives in the second photodiode 12 via the beam path 25, and light from the second light-emitting diode 5 arrives in the first photodiode 11 via the beam path 24. The first light-emitting diode 3 and the second light-emitting diode 5 preferably transmit equal amounts of light, at least approximately and averaged over time, such that the optical path from the first light-emitting diode 3 to the first photodiode 11 has at least approximately the same properties as the optical path from the second light-emitting diode 5 to the second photodiode 12. Moreover, the first photodiode 11 should have at least approximately the same transducer constant, i.e. the same efficiency in terms of light detection, as the second photodiode 12. If the item 21 is homogeneous and sufficiently large, the same current level will be generated in the first photodiode 11, at least approximately and averaged over time, as in the second photodiode 12.

Figure 3:
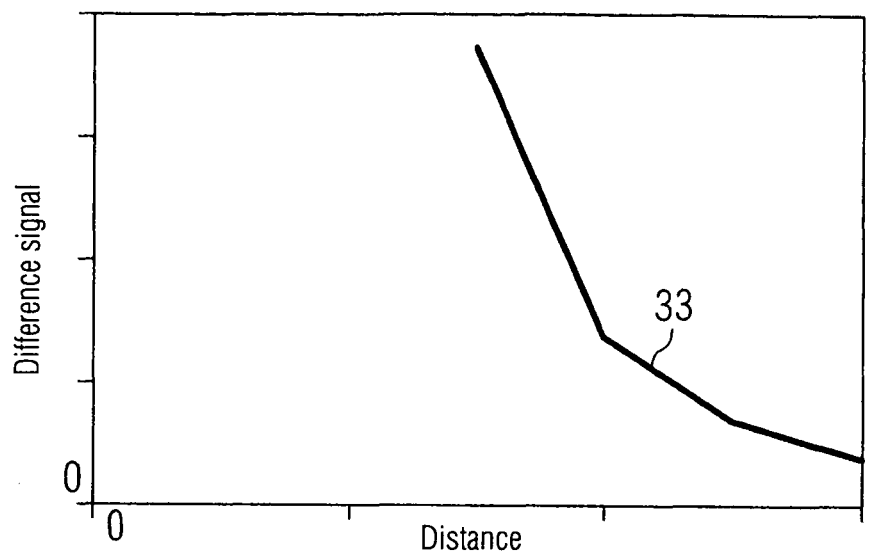
FIG. 3 shows a experimentally measured dependency of a measured difference signal on the distance of an identified object from the sensor apparatus.

FIG. 3 shows how the difference signal of the sensor apparatus illustrated in FIGS. 1 and 2 changes if an identified object moved towards or away from the sensor apparatus. In the illustrated system of coordinates, the distance of the object to the sensor apparatus is plotted on the X-axis, wherein the zero point is situated at the left-hand end of the axis and is also designated accordingly. The scaling is arbitrary. The difference signal is plotted on the Y-axis, the zero point being likewise situated at the bottom end of the scale and again being designated accordingly. The scaling has been chosen arbitrarily here also.

It is clearly visible from FIG. 3 that the difference signal increases very markedly as soon as the distance of the object to the sensor apparatus falls below a specific limit. The sensor apparatus is therefore very suitable for use as a proximity alarm, as in the automatic opening of doors, for example.

Since the sensor apparatus has very little sensitivity in respect of far distant items, the sensor apparatus is also particularly suitable as an intrusion alarm, which can be used to protect valuable items that are situated in a container such as a showcase, for example. A sensor apparatus of the type described above will therefore be influenced only slightly by the walls and the glass panels of the showcase.

The described sensor apparatus cannot be used to report fixed items, however, but can also recognize liquids, gases and aerosols having defined optical properties, and therefore also e.g. smoke. The functional principle described above can therefore also be applied to a smoke alarm.

Figure 4:
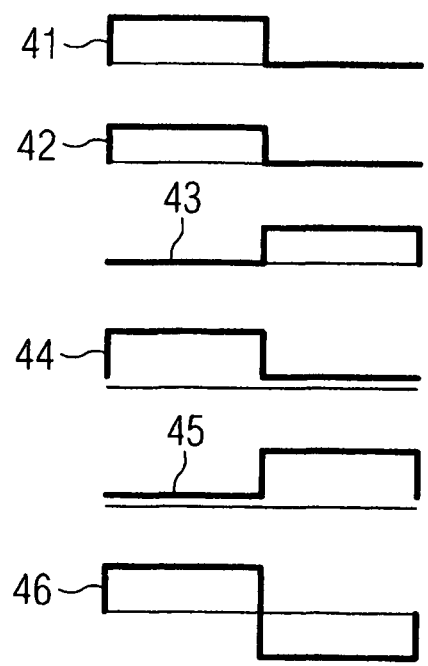
FIG. 4 shows the temporal profile of a plurality of voltages and currents in the sensor apparatus as illustrated in FIGS. 1 and 2.

FIG. 4 shows the temporal profile of a plurality of voltages and currents in the case of the sensor apparatus illustrated in FIGS. 1 and 2. A first signal 41 corresponds to the temporal profile of the voltage which is output by the signal source 1 (see FIGS. 1 and 2). The second signal 42 corresponds to the current which flows through the first light-emitting diode 3. The third signal 43 corresponds to the current which flows through the second light-emitting diode 5. The fourth signal 44 corresponds to the current which is generated by the first photodiode 11 as a result of a detection of light. The fifth signal 45 corresponds to the current which is generated by the second photodiode 12 as a result of a detection of light. The magnitude of the currents that are generated by the photodiodes 11 and 12 depends on the quantity of the light that is emitted by the light-emitting diodes 3 and 5 and on the size and reflective response of the object to be recognized. In this case, it is assumed in FIG. 4 that an object of this size is present and therefore a perceptible current is produced in the two photodiodes 11 and 12. However, this current is not so great in either case that any component is operated beyond its linear working range.

Within the period during which current flows through the first light-emitting diode 3, a relatively large current will flow in the first photodiode 3. By contrast, within the period during which current flows in the second light-emitting diode 5, relatively little current or no current at all will flow in the first photodiode 3. The reason for this is that the light which is transmitted by the second light-emitting diode 5 and backscattered by the object 6, as explained above, preferably arrives in the second photodiode 12 and to a considerably lesser extent in the first photodiode 11.

In a similar manner, within the period during which current flows through the second light-emitting diode 5, a relatively large current is generated by the second photodiode 12. Within the period in which current flows through the first light-emitting diode 3, a relatively small current is generated by the second photodiode 12.

The sixth signal 46 illustrated in FIG. 4 corresponds to the current between the connection lines 13 and 14. Since the two photodiodes 11 and 12 are wired in an antiparallel manner, this current is equal to the difference of the currents in the two photodiodes 13 and 14. In this case, it is assumed that this difference is positive when the current of the first photodiode 11 is greater than the current of the second photodiode 12. However, the choice of operational sign is arbitrary and has no significance in relation to the function of the described sensor apparatus. The current between the connection lines 13 and 14 is positive when current flows through the first light-emitting diode 3. By contrast, this current is negative and of approximately the same magnitude when the current flows through the second light-emitting diode 5. Consequently, a current whose shape is at least approximately and whose direct-current part is at least approximately zero is applied to the input of the difference amplifier 15. The same also applies to the output voltage of the difference amplifier 15, said output voltage being supplied to the evaluation unit 16.

Figure 5:
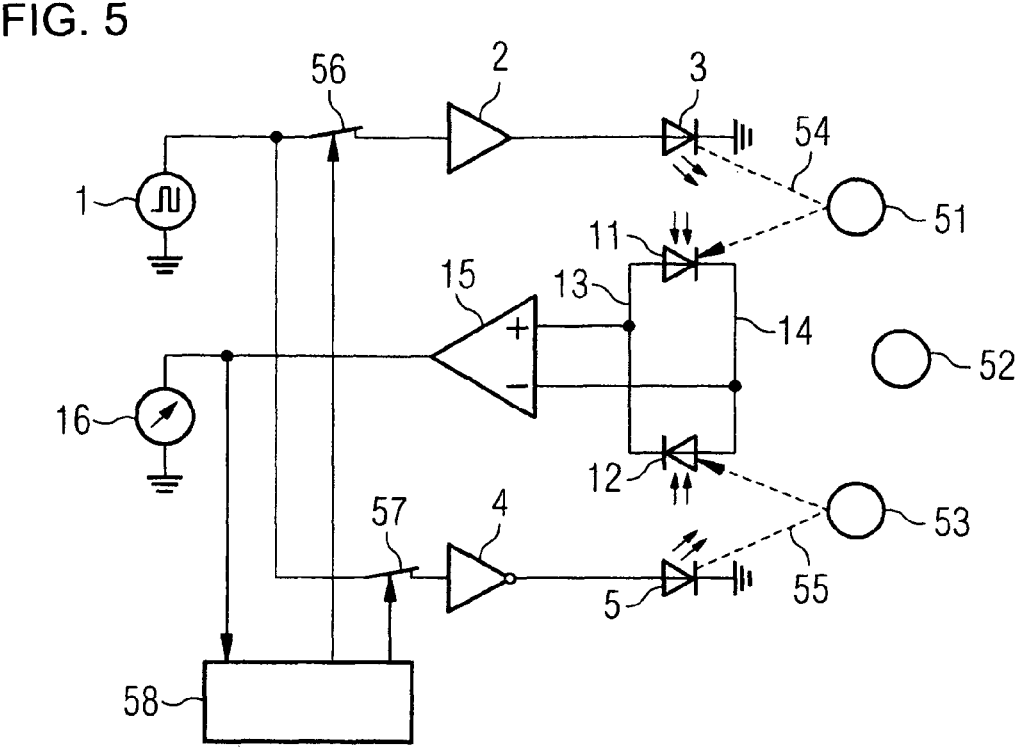
FIG. 5 shows a sensor apparatus according to a second exemplary embodiment of the invention and comprising two switch elements, wherein a transmitting device can be selectively deactivated by opening a switch element in each case.

It can also occur that a plurality of small objects are present. This is shown in FIG. 5, in which a sensor apparatus according to a second exemplary embodiment of the invention is illustrated. In comparison with the sensor apparatus illustrated in FIGS. 1 and 2, this sensor apparatus additionally features two switch elements, wherein a light-emitting diode can be selectively deactivated by opening a switch element.

Various scenarios are described below, a small object (not illustrated) being situated at various positions in each case, and said positions being designated by the reference signs 51, 52 and 53. These positions 51, 52, 53 are obviously only exemplary, and the object can also be situated at any other position. Likewise, a plurality of small objects can also be present simultaneously in the detection region of the sensor apparatus.

If a small object is situated in the position 51, light from the first light-emitting diode 3 arrives in the first photodiode 11 via the beam path 54. By contrast, of the light that is emitted by the second light-emitting diode 5, none or only a very small portion arrives in the second photodiode 12.

Figure 6:
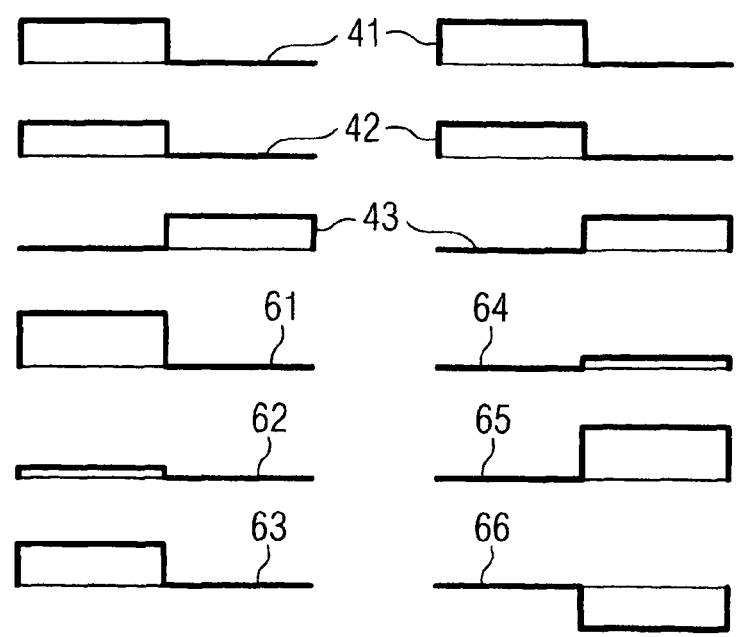
FIG. 6 shows the temporal profile of a plurality of voltages and currents in the sensor apparatus as illustrated in FIG. 5.

The signals that are produced in the sensor apparatus as a result of this are illustrated in FIG. 6. The rectangular voltage of the signal source 1 is designated by the reference sign 41. For ease of understanding, this signal is drawn in twice, i.e. in the left-hand column and in the right-hand column of FIG. 6. The current through the first light-emitting diode 3 corresponds to the signal 42, and the current through the second light-emitting diode 5 corresponds to the signal 43. The signals 42 and 43 are also drawn in twice.

If the small object is situated in the position 51, a relatively large amount of light from the first light-emitting diode 3 arrives at the first photodiode 11, and therefore a relatively large current is produced there. This current is designated as signal 61 and is temporally in phase with the current 42 through the first light-emitting diode 3. By contrast, only a small amount of light arrives in the second photodiode 12, and therefore this current is small as illustrated by the signal 62. Signal 63 shows the total current at the input of the difference amplifier 15. This current corresponds to the difference of the currents 61 and 62, wherein the first current 61 is treated as positive and the second current 62 as negative. The difference current 63 is temporally in phase with the current 42 through the first light-emitting diode 3 and has a positive direct-current part.

If a small object is situated at the position 53, a relatively large amount of light from the second light-emitting diode 5 arrives at the second photodiode 12. A relatively large current is then generated by the second photodiode 12, wherein said current is designated as signal 65 and is in opposite phase to the current 42 through the first light-emitting diode. By contrast, only a small amount of light arrives in the first photodiode 11, and therefore the corresponding current is small, as illustrated by the signal 64. The signal 66 shows the total current at the input of the difference amplifier 15. This difference current 66 in turn corresponds to the difference of the currents 61 and 62. The difference current 66 is likewise temporally in phase with the current 43 through the second light-emitting diode 5, but it does not have a negative direct-current part.

If a large object is present, the difference of the currents from the photodiodes 11, 12 will likewise be temporally in phase with the current 42 through the first light-emitting diode 3. The direct-current part is however relatively small or even disappears, as illustrated by the signal 46 (see FIG. 4).

A small object in the central position 52 essentially generates no output signal. This behavior of the sensor apparatus is not only permissible but also desirable.

It applies generally that the ratio of the direct-current part to the amplitude of the difference signal can give an indication of the size of the object that is to be recognized, wherein it can be ruled out in particular that an individual small object results in a signal having a large amplitude and a small direct-current part. The speed at which this ratio changes can give an indication of the speed of the object, and the operational sign can give an indication of the position of the object. Consequently, the evaluation unit 16 is able to draw conclusions about a recognized object by analyzing the output signal of the amplifier 15. However, the amplifier 15 must also be able to amplify direct-current signals for this.

It is also possible to draw conclusions about the size of the object to be recognized if the light-emitting diodes 3 and 5 are individually switched off. The switch elements required for this purpose are likewise shown in FIG. 5 and denoted by the reference signs 56 and 57. According to the particularly preferred exemplary embodiment illustrated here, the first switch element 56 is provided for the purpose of interrupting the signal flow from the signal source 1 to the first light-emitting diode 3. Although the switch element 56 is drawn in front of the amplifier 2, it can be situated at any desired location on the signal path between the signal source 1 and the first light-emitting diode 3. In the same way, a second switch element 57 is provided for the purpose of interrupting the signal flow from the signal source 1 to the second light-emitting diode 5.

Provision is further made for a control apparatus 58, which is also supplied with the output signal of the signal source 1 and, on the basis of the properties of this output signal and other input variables, operates the switch elements 56 and 57. The switching states of the switch elements 56 and 57 can therefore be cyclically varied by means of the control apparatus 58, wherein both switch elements 56 and 57 are closed in a first operating state, only the switch element 56 is closed in a second operating state, and only the switch element 57 is closed in a third operating state.

If a large difference signal is received while switch elements 56 and 57 are closed, there is either a large object or a small object in front of the first light-emitting diode 3 in the position designated as 51, or a small object in front of the second light-emitting diode 5 in the position designated as 53. If the size of the difference signal after opening the first switch element 56 decreases to approximately half its previous value, the object must be a large object. If the size of the difference signal after opening the first switch element 56 disappears completely or largely, the object that is situated in the position designated as 51 must be a small object. If the difference signal remains approximately the same, the object that is situated in the position 53 must be a small object.

Using the second switch element 57, it is likewise possible analogously to establish whether there is a large object or a small object in the position 51, or a small object in the position 53.

Since fundamentally the same information is obtained using the two switch elements 56 and 57, an embodiment is possible in which only one switch element is present. However, since the provision of the second switch element does not generally result in a significant additional cost in instrumentation, and allows the size and position of the object to be identified with greater certainty, the illustrated embodiment with two switch elements is preferred. This also applies if more than two light-emitting diodes are present, an embodiment then being preferred in which each light-emitting diode can be switched off individually.

Small objects can be insects, for example. There is no immediately impending hazard from insects, and it is therefore not necessary to trigger an alarm. Insects do nonetheless represent a hazard, however, since they could damage the contents that are displayed in a showcase, for example. Consequently, it can also be useful to output a warning to the user if only small objects are detected by the sensor apparatus.

During the operation of a photoelectrical proximity alarm or hazard alarm, the hazard exists that extraneous light such as e.g. sunlight or the light from artificial light sources arrives in the photodiode (or photodiodes). This (or these) can then be overridden and the function of the sensor apparatus can be compromised thus. Measures that can reduce the influence of extraneous light are obviously known to a person skilled in the art. Such measures comprise e.g. mounting a suitable filter in front of the photodiode, such that only light of a defined wavelength, which is preferably different to that of the interference source, can pass through. Furthermore, the measuring signal can be modulated in such a way that its time response differs from all conceivable interference sources if possible. A proximity or hazard alarm which is constructed in accordance with the above principles can therefore achieve an additional suppression of such interferences without the need for further switch elements and/or measures.

Figure 7:
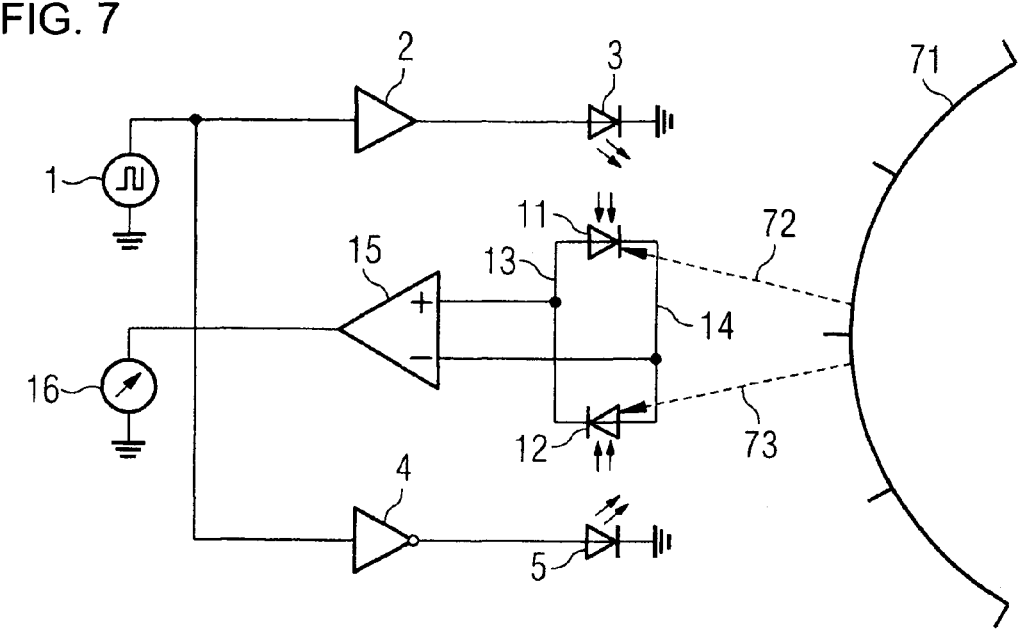
FIG. 7 shows the sensor apparatus as illustrated previously in FIGS. 1 and 2, during the detection of a remote and highly luminous item.

FIG. 7 shows the sensor apparatus as illustrated in FIGS. 1 and 2 during the detection of a remote and highly luminous item 71. The item can be the sun, for example. The item 71 emits beams which inter alia arrive in the first photodiode 11 via the beam path 72, and in the second photodiode 12 via the beam path 73. If the distance of the radiating item 71 from the sensor apparatus is sufficiently great and the radiation characteristics are sufficiently homogeneous, the energy that arrives in the two photodiodes 11 and 12 via the two beam paths 72 and 73 will be largely equal. Consequently, the output current of the two photodiodes 11 and 12 is also largely equal. As a result of the two photodiodes 11 and 12 being wired in an antiparallel manner via the connection lines 13 and 14, their individual currents largely cancel each other out, such that only a small amount of current flows in the input of the difference amplifier 15 and only a very small voltage arises at the output of this amplifier 15.

It is particularly appropriate to use at least one PIN diode 12 for the photodiode 11 and/or for the photodiode 12. PIN diodes actually have a particularly low impedance and therefore without difficulty can process even large currents that originate from strong signal sources.

In certain application scenarios, it can be desirable if the difference current can be balanced to zero in the quiescent state. This applies in particular if the sensor apparatus is expected to respond in a particularly sensitive manner to intruding items.

Figure 8:
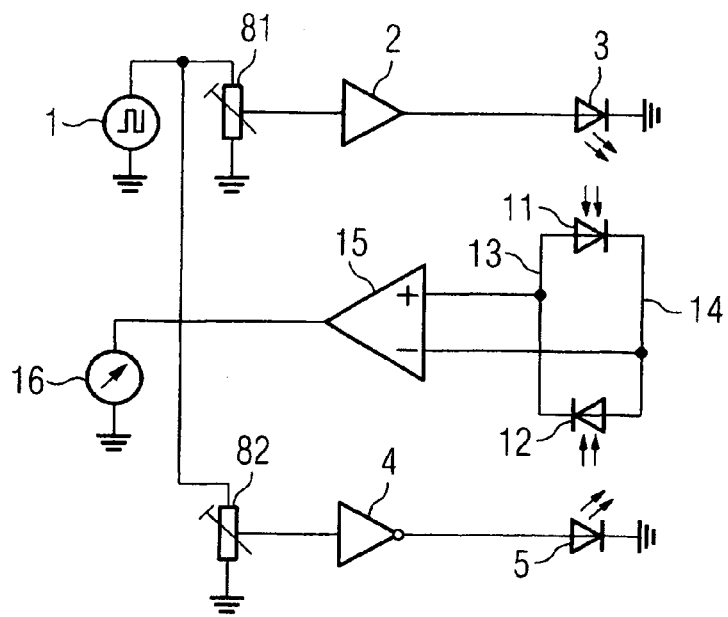
FIG. 8 shows a sensor apparatus as per a third exemplary embodiment of the invention, comprising two adjustable balancing elements for balancing the difference signal to a predefined value.

In accordance with a third exemplary embodiment of the invention, FIG. 8 shows a sensor apparatus comprising two adjustable balancing elements 81 and 82 for balancing the difference signal to a predefined value. The balancing element 81 is situated in the signal path from the signal source 1 to the first light-emitting diode 3 and before the non-inverting amplifier 2. The balancing element 82 is situated in the signal path from the signal source 1 to the second light-emitting diode 5 and before the inverting amplifier 4. These balancing elements 81 and 82 can be balanced with the aid of a suitable algorithm, such that the difference current at the input of the amplifier 15 in the quiescent state is zero or assumes another desired value.

It should be noted that both balancing elements 81 and 82 need not be present. Rather, it is sufficient for one balancing element to be present on one of the signal paths from the signal source 1 to the first light-emitting diode 3 or from the signal source 1 to the second light-emitting diode 5. Likewise, the balancing element need not be arranged at the marked location. The balancing element can be arranged at any desired location between the signal source 1 and the first light-emitting diode 3 or the second light-emitting diode 5. However, the embodiment illustrated in FIG. 8 has circuit-related advantages in that (a) the balancing elements 81 and 82 can be constructed in such a way that they need only lessen and not amplify, and (b) the balancing elements 81 and 82 are installed at a location where the power of the signals is low, and therefore this circuit can be realized simply and economically.

It should additionally be noted that balancing is also possible on the reception path between the two photodiodes 11 and 12 and the amplifier 15.

Figure 9:
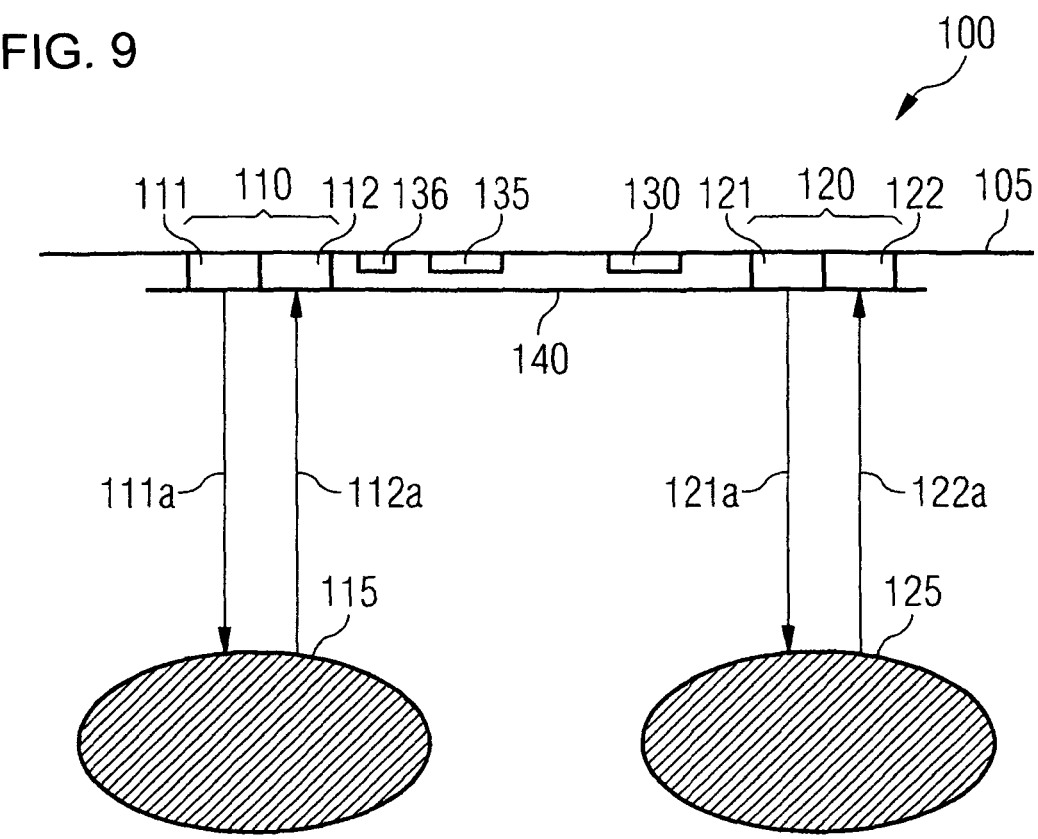
FIG. 9 shows a schematic cross-sectional illustration of a smoke alarm comprising two reflective light barriers which are mounted on a shared printed circuit board.

FIG. 9 shows a smoke alarm 100 which features a base plate 105. According to the exemplary embodiment illustrated here, the base plate is a printed circuit board 105 or a suitable circuit support for accommodating electronic and optoelectronic components. All of the components mounted on the printed circuit board 105 are contacted in a suitable manner, which is not shown, by means of conductive tracks or electrical wire connections.

The smoke alarm 100 comprises a first reflective light barrier 110 and a second reflective light barrier 120. The first reflective light barrier 110 features a first light transmitter 111 and a first light receiver 112 which is arranged immediately adjacent thereto in a shared housing. The second reflective light barrier 120 features a second light transmitter 121 and a second light receiver 122 which is arranged immediately adjacent thereto in a shared housing.

The first light transmitter 111 emits a first illumination light 111a in an essentially perpendicular direction relative to the plane of the printed circuit board 105. The first illumination light 111a is at least partially backscattered by approximately 180° in a first detection space 115, in which e.g. smoke is located. The backscattered light reaches the first light receiver 112 as first measured light 112a.

Correspondingly, the second light transmitter 121 emits a second illumination light 121a in an essentially perpendicular direction relative to the plane of the printed circuit board 105. The second illumination light 121a is at least partially backscattered by approximately 180° in a second detection space 125, in which e.g. smoke is located. The backscattered light reaches the second light receiver 122 as second measured light 122a.

The smoke alarm 100 additionally features a subtraction unit 136, which works out a difference signal from the output signals of the two light receivers 112 and 122. This difference signal is supplied to a data processing device 135 of the smoke alarm 100.

Provision is further made for a control device 130, this being coupled to the two light transmitters 111 and 121. As a result of this, the two light transmitters 111 and 121 can be activated or switched on independently of each other.

All of the components 110, 120, 130, 135 and 136 of the smoke alarm 100 are mounted on the printed circuit board 105 and electrically contacted in a suitable manner. The smoke alarm 100 can therefore be realized in a very flat structural shape. In this case, the height of the smoke alarm 100 is defined solely by the thickness of the printed circuit board 105 and by the components 110, 120, 130, 135 and 136.

According to the exemplary embodiment illustrated here, all of the components 110, 120, 130, 135 and 136 are so-called Surface Mount Technology (SMD) parts. It is therefore possible to achieve an overall height of just 2.1 mm, for example. In this case, the overall height is derived from the distance between the top side of the printed circuit board 105 and the bottom surface of the smoke alarm, said bottom surface being denoted by the reference sign 140 in FIG. 1.

According to the exemplary embodiment illustrated here, the light-active surfaces of the light transmitters 111, 121 and of the light receivers 112, 122 coincide with the surface 140. This means that no further parts of the smoke alarm 100 are situated between these light-active surfaces and the relevant detection space 115, 125. This also applies to covers or housing parts. Such covers, which are frequently provided for the purpose of dirt protection in the case of known smoke alarms, are however not at all necessary in many applications, particularly in the domestic environment. Use can also be made of light barriers which already feature transparent protective layers for the light-active surfaces of the light transmitters 111, 121 and the light receivers 112, 122, such that at least a certain protection against soiling is provided thus.

The described smoke alarm 100 comprising two reflective light barriers that are aligned in parallel with each other has the advantage that it does not feature any optical elements such as e.g. lenses or mirrors. Consequently, the smoke alarm can be manufactured in a particularly simple manner using economical components. During the construction or assembly of the smoke alarm, there is also no need to observe special assembly tolerances. All of the components required for the smoke alarm are mass-produced products which can be procured economically.

It should be noted that, as a result of the parallel light beams 111a, 112a, 121a, 122a, the hazard exists in principle that very distant fixed objects could be interpreted as smoke. A physical object that is inadvertently brought into the detection space in the vicinity of the smoke alarm 100 can clearly be distinguished from a smoke signal on the basis of the very strong backscatter signal. However, very distant scattering objects which are situated in the field of view of the smoke alarm only deliver a weak signal due to their generally diffuse backscattering, and often can no longer reliably be distinguished from smoke using the above criterion.

A reliable distinction between smoke and very distant physical scattering objects can however be made in an effective manner using the described smoke alarm 100 by e.g. switching off or deactivating the other light transmitter 121 while the illumination light 110a is being transmitted by the activated light transmitter 111. Both light receivers 112 and 122 are activated at the same time. If both light receivers 112 and 122 show at least approximately the same signal in this case, it is a remote echo from an item, which is situated outside of the detection space in the field of view of the smoke alarm. This echo can originate e.g. from a floor surface of the space that is monitored by the smoke alarm 100, and not from smoke particles. Smoke particles would actually also be found at least to some extent in the vicinity of the smoke alarm 100, particularly if the smoke alarm 100 was mounted on the ceiling, and therefore the signals of the two light receivers 112 and 122 would have different strengths in this case.

In order to detect smoke, it is also possible simply to evaluate the difference signal between the two light receivers 112 and 122. In this case, the influence of extraneous light can also be effectively suppressed.

Figure 10:
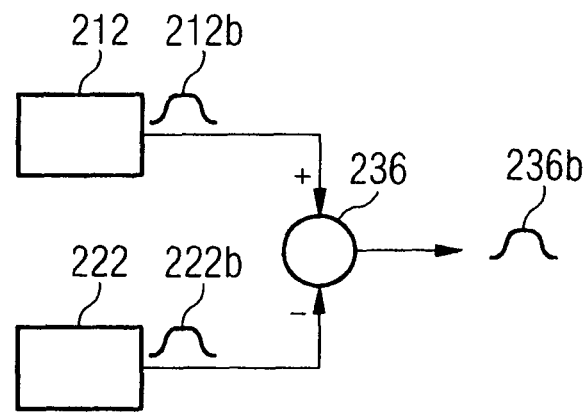
FIG. 10 shows a subtraction unit for working out a difference signal between two output signals from the light barriers as illustrated in FIG. 9.

FIG. 10 shows the subtraction unit which was previously illustrated in FIG. 9 and is now denoted by the reference sign 236. A first output signal 212b of the first light receiver, which is denoted in FIG. 10 by the reference sign 212, is supplied to a "plus input" of the subtraction unit 236. A second output signal 222b of the second light receiver, which is denoted in FIG. 10 by the reference sign 222, is supplied to a "minus input" of the subtraction unit 236. From the two output signals 212b and 222b, a difference signal 236b is worked out and supplied to a data processing device which is not shown in FIG. 10. The difference signal 236b can be evaluated in the data processing device as described above.

Figure 11:
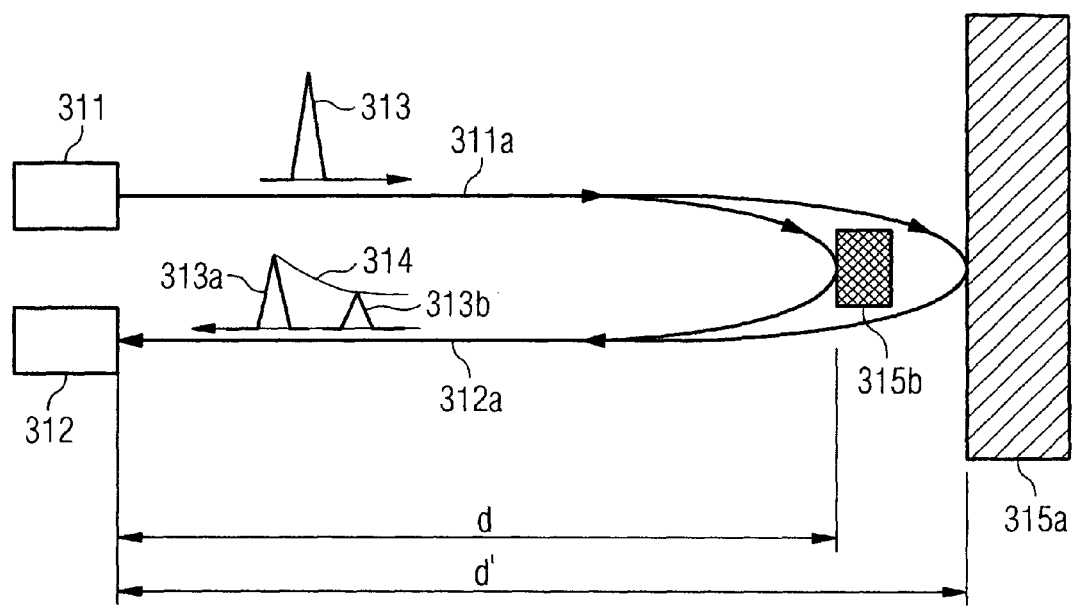
FIG. 11 illustrates a temporal widening or structuring of a light pulse as a result of the scattering at two items which are at different distances from the smoke alarm.

In a schematic representation, FIG. 11 illustrates the temporal widening or structuring of a light pulse as a result of the scattering at various spatially distributed items 315a and 315b. The items 315a and 315b are specifically not smoke. With reference to the degree of temporal widening or temporal structuring, it is possible to draw conclusions relating to the spatial distribution of the physical scattering objects 315a and 315b.

As shown in FIG. 11, a light transmitter 311 transmits an illumination light 311a which comprises at least one short light pulse 313. This light pulse 313 is then backscattered by approximately 180 degrees at items 315a and 315b in the field of view of the alarm. In this case, the backscattering at all possible items occurs within the field of view of the alarm 311, 312. For reasons of clarity, however, only two items are taken into consideration in the illustration in FIG. 11. One exemplary item 315b is situated at a distance d from the light transmitter 311, while the other exemplary item 315a is situated at a distance d' from the light transmitter 311. According to the exemplary embodiment illustrated here, the item 315a is the floor of a monitored space. The item 315b can be any item such as a piece of furniture, for example, which is situated permanently or temporarily between the floor 315a and the smoke alarm 311, 312.

The light pulse 313 first strikes the second item 315b at a distance d from the light transmitter. Part of the light energy is backscattered in this case, such that the measured light 312a which strikes the light receiver 312 features a first backscatter pulse 313a. Subsequently, the meanwhile somewhat weakened light pulse 313 strikes the first item or the floor 315a, which is situated at the distance d' from the light transmitter. Part of the light energy is again backscattered at the floor 315a, such that the measured light 312a features a second backscatter pulse 313b.

If all relevant items are taken into consideration, a superimposition of numerous individual backscatter pulses is therefore produced, the resulting total backscatter pulse being widened significantly in comparison with the initial light pulse 313. As a result of the absorption by any smoke which is situated in the field of view of the alarm, the intensity of the later backscatter pulses can be reduced in this case in comparison with the earlier backscatter pulses striking the light receiver 312. This produces an asymmetrical shape or an asymmetrical temporal profile of the total backscatter pulse, this being denoted in FIG. 11 by the reference sign 314.

In this context, it should be noted that any smoke which is situated in the field of view of the alarm and is situated at a distance of typically more than a few centimeters from the smoke alarm 311, 312 does not make a significant contribution to the received optical backscatter signal.

In order to detect the above described effect of the widening or structuring of the backscatter signal, not only the amount or strength of the backscattering but also the temporal profile of the corresponding pulsed backscatter signal can be evaluated for the purpose of intelligent smoke detection. As already suggested above, each initial light pulse 313 in this case can generate a plurality of backscatter pulses 313a, 313b, etc. which originate from the spatially distributed items 315a, 315b. The more distant an item, the more the emitted light beam 311a is attenuated as a result of scattering and absorption by smoke particles that are possibly present in the room air. The same occurs in respect of the backscattered measured light 312a. However, the echo of the more distant items also arrives later at the light receiver 312. On the basis of the temporal profile of the received light pulse, it is therefore possible to identify the spatial distribution or arrangement of the items that are situated in the field of view of the smoke alarm.

It should be noted that it is also possible to calculate the propagation time of the light pulse, measured from the transmission to the receipt of the backscattered light pulse 314, and hence the distance between the light transmitter 311 or the light receiver 312 and the items 315a and 315b.

LIST OF REFERENCE SIGNS

1 Signal source/function generator
2 Non-inverting amplifier
3 First optical transmitting device/first light-emitting diode
4 Inverting amplifier
5 Second optical transmitting device/second light-emitting diode
6 Object
7 First transmission radiation/first transmitted light
8 Second transmission radiation/second transmitted light
11 First receiving device/first photodiode
12 Second receiving device/second photodiode
13 Electrical line
14 Electrical line
15 Difference amplifier
16 Evaluation unit
21 Item (reflective)
22 Beam path
23 Beam path
24 Beam path
25 Beam path
33 Measuring curve
41 Voltage profile for signal source 1
42 Current profile through first light-emitting diode 3
43 Current profile through second light-emitting diode 5
44 Current from first photodiode 11
45 Current from second photodiode 12
46 Difference current
51 Object position
52 Object position
53 Object position
54 Beam path
55 Beam path
56 Switch element
57 Switch element
58 Control apparatus
61 Current signal from first photodiode 3
62 Current signal from second photodiode 5
63 Difference current
64 Current from first photodiode 11
65 Current from second photodiode 12
66 Difference current
71 Item (remote and highly luminous)/sun
72 Beam path
73 Beam path 81 Balancing element
82 Balancing element
100 Sensor apparatus/smoke alarm
105 Base plate/printed circuit board
110 First reflective light barrier
111 First transmitting device/first light transmitter
111a First transmission radiation/first illumination light
112 First receiving device/first light receiver
112a First reception radiation/first measured light
115 First detection space/first scatter volume
120 Second reflective light barrier
121 Second transmitting device/second light transmitter
121a Second transmission radiation/second illumination light
122 Second receiving device/second light receiver
122a Second reception radiation/second measured light
125 Second detection space/second scatter volume
130 Control device
135 Evaluation device/data processing device
136 Subtraction unit
140 Surface
212 First receiving device/first light receiver
212b First output signal
222 Second receiving device/second light receiver
222b Second output signal
236 Subtraction unit
236b Difference signal
311 Transmitting device/light transmitter
311a Transmission radiation/illumination light
312 Receiving device/light receiver
312a Reception radiation/measured light
313 Radiation pulse/light pulse
313a Backscatter pulse
313b Backscatter pulse
315a First item/floor
315b Second item

The invention claimed is:

1. A sensor apparatus for optically detecting an object, the sensor apparatus comprising:
   a base plate;
   a first detection space;
   a first light transmitter configured for emitting a first illumination light, said first light transmitter mounted on said base plate;
   a first light receiver configured for receiving a first measurement light formed from at least a partial backscattering of the first illumination light by the object in said first detection space, said first light receiver mounted on said base plate adjacent said first light transmitter, said first light receiver configured for outputting a first output signal;
   a second light transmitter configured for emitting a second illumination light, said second light transmitter mounted on said base plate;
   a second detection space;
   a second light receiver configured for receiving a second measurement light formed from at least a partial backscattering of the second illumination light by the object in said second detection space said second light receiver mounted on said base plate adjacent said second light transmitter, said second light receiver configured for outputting a second output signal;
   at least one of the first measurement light and the second measurement light including a scattered light produced by partial or complete scattering of the first illumination light at the object;
   a subtraction unit having an input side coupled to said first light receiver and said second light receiver, and an output side providing a difference signal formed by a difference between the first output signal of said first light receiver and the second output signal of said second light receiver; and
   an evaluation unit connected to said output side of said subtraction unit to receive the difference signal between the first output signal of said first light receiver and the second output signal of said second light receiver.

2. The sensor apparatus according to claim 1, wherein one or both of the following is true:
   said first light transmitter and said first light receiver are formed as a first reflective light barrier; and
   said second light transmitter and said second light receiver are formed as a second reflective light barrier.

3. The sensor apparatus according to claim 1, wherein one or both of the following is true:
   a direction of the first illumination light is inclined relative to a normal of said base plate in a direction towards said first light receiver; and
   a direction of the second illumination light is inclined relative to the normal of said base plate in a direction towards said second light receiver.

4. The sensor apparatus according to claim 1, wherein the direction of the first illumination light and the direction of the second illumination light run parallel to one another.

5. The sensor apparatus according to claim 1, wherein said first light transmitter and a second light transmitter and said first light receiver and said second light receiver each form an external boundary of the sensor apparatus.

6. The sensor apparatus according to claim 1, wherein said first light receiver is configured for detecting a temporal profile of the first illumination light.

7. The sensor apparatus according to claim 6, wherein said first light transmitter is configured for emitting a pulsed first illumination light.

8. The sensor apparatus according to claim 6, further comprising a control device connected to said first light transmitter and said second light transmitter, said control device configured to activate said first light transmitter independently of said second light transmitter.

9. A method for detecting smoke, which comprises:
   providing a sensor apparatus for optically detecting an object, the sensor apparatus including:
   a base plate;
   a first detection space;
   a first light transmitter configured for emitting a first illumination light, the first light transmitter mounted on the base plate;
   a first light receiver configured for receiving a first measurement light formed from at least a partial backscattering of the first illumination light by the object in the first detection space, the first light receiver mounted on the base plate adjacent the first light transmitter, the first light receiver configured for outputting a first output signal;
   a second light transmitter configured for emitting a second illumination light, the second light transmitter mounted on the base plate; a second detection space;
   a second light receiver configured for receiving a second measurement light formed from at least a partial backscattering of the second illumination light by the object in the second detection space the second light receiver mounted on the base plate adjacent the second light transmitter, the second light receiver configured for outputting a second output signal;

at least one of the first measurement light and the second measurement light including a scattered light produced by partial or complete scattering of the first illumination light at the object;

a subtraction unit having an input side coupled to the first light receiver and the second light receiver, and an output side providing a difference signal formed by a difference between the first output signal of the first light receiver and the second output signal of the second light receiver; and an evaluation unit connected to the output side of the subtraction unit to receive the difference signal between the first output signal of the first light receiver and the second output signal of the second light receiver;

sending at least the first illumination light from the first light transmitter; and receiving at least the first measurement light at the first light receiver.

10. The method according to claim 9, which further comprises receiving at least the second measurement light at the second light receiver.

11. The method according to claim 9, which further comprises forming the difference signal by taking the difference between the first output signal and the second output signal.

12. The method according to claim 9, which further comprises emitting the first illumination light from the first light transmitter as light pulses.

13. The method according to claim 12, which further comprises measuring a length of the first measurement light.

14. The method according to claim 12, which further comprises measuring a time between an emission of a light pulse of the first illumination light from the first light transmitter and a reception of a corresponding light pulse of the first measurement light by the first light receiver.

* * * * *